(12) United States Patent
Levetan

(10) Patent No.: US 10,010,578 B2
(45) Date of Patent: *Jul. 3, 2018

(54) INSULIN INDEPENDENCE AMONG PATIENTS WITH DIABETES UTILIZING AN OPTIMIZED HAMSTER REG3 GAMMA PEPTIDE

(71) Applicant: Claresa Levetan, Bryn Mawr, PA (US)

(72) Inventor: Claresa Levetan, Bryn Mawr, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/094,413

(22) Filed: Apr. 8, 2016

(65) Prior Publication Data

US 2016/0213740 A1 Jul. 28, 2016

Related U.S. Application Data

(60) Division of application No. 14/453,414, filed on Aug. 6, 2014, now Pat. No. 9,321,812, which is a continuation of application No. 14/453,421, filed on Aug. 6, 2014.

(60) Provisional application No. 61/971,721, filed on Mar. 28, 2014.

(51) Int. Cl.
| | |
|---|---|
| *A61K 38/00* | (2006.01) |
| *A61K 38/17* | (2006.01) |
| *C07K 7/08* | (2006.01) |
| *A61K 38/10* | (2006.01) |
| *A61K 38/13* | (2006.01) |
| *A61K 47/48* | (2006.01) |
| *A61K 45/06* | (2006.01) |
| *C07K 14/47* | (2006.01) |
| *A61K 38/21* | (2006.01) |

(52) U.S. Cl.
CPC .......... *A61K 38/1709* (2013.01); *A61K 38/10* (2013.01); *A61K 38/13* (2013.01); *A61K 38/1732* (2013.01); *A61K 38/212* (2013.01); *A61K 45/06* (2013.01); *A61K 47/48215* (2013.01); *C07K 7/08* (2013.01); *C07K 14/474* (2013.01)

(58) Field of Classification Search
CPC .... A61K 2300/00; A61K 38/10; A61K 38/13; A61K 38/1732; A61K 38/212; A61K 39/395; A61K 38/1709; A61K 45/06; A61K 47/48215; C07K 14/474; C07K 7/08

See application file for complete search history.

(56) References Cited

U.S. PATENT DOCUMENTS

| | | | | |
|---|---|---|---|---|
| 5,571,507 | A * | 11/1996 | Rubin-Kelley | A61K 38/164 424/85.2 |
| 5,580,855 | A | 12/1996 | Ferreira et al. | |
| 7,214,661 | B2 | 5/2007 | Carney | |
| 8,431,524 | B2 | 4/2013 | Savio et al. | |
| 8,816,047 | B2 * | 8/2014 | Levetan | C07K 14/4733 530/327 |
| 2004/0132644 | A1 * | 7/2004 | Vinik | C07K 14/474 514/7.3 |
| 2010/0022445 | A1 | 1/2010 | Scheiflinger et al. | |
| 2011/0143999 | A1 | 6/2011 | Zhang et al. | |
| 2012/0183582 | A1 | 7/2012 | Mehta et al. | |
| 2016/0002310 | A1 * | 1/2016 | Rosenberg | C07K 14/4733 514/6.9 |
| 2016/0039875 | A1 * | 2/2016 | Levetan | A61K 38/1709 424/278.1 |
| 2016/0039876 | A1 * | 2/2016 | Levetan | A61K 38/1709 424/278.1 |
| 2016/0206682 | A1 * | 7/2016 | Levetan | A61K 38/1709 |
| 2016/0206683 | A1 * | 7/2016 | Levetan | A61K 38/1709 |
| 2016/0213741 | A1 * | 7/2016 | Levetan | A61K 38/1709 |
| 2016/0213746 | A1 * | 7/2016 | Levetan | A61K 38/1709 |

OTHER PUBLICATIONS

Bieong-Kil et al. Homodimeric SV40 NLS peptide formed by disulfide bond as enhancer for gene delivery. Biorganic and Medicinal Chemistry Letters, 2012. vol. 22, pp. 5415-5418.*
Technical Information N-Terminal Acetylation and C-Terminal Amidation of Peptides (Thermo, 2004).*
Tanaka-Kataoka et al. Oral Use of Interferon-a Delays the Onset of Insulin-Dependent Diabetes Mellitus in Nonobese Diabetes Mice. J Interferon Cytokine Research, 1999, pp. 877-879 (Year: 1999).*
Edelman, David; How We May Restore Insulin Production in Type 1 Diabetes; May 2013; https://www.diabetesdaily.com/blog/2013/05/how-we-may-restore-insulin-production-in-type-1-diabetes.
R. E. Ratner et al.; Double-Blind, Placebo-Controlled Trial of Islet Neogenesis Gene Associated Protein (INGAP) in Type 1 Diabetes (T1DM) Subjects; 2005; http://professional.diabetes.org/Abstracts_Display.aspx?CID=52536.
Rosenberg et al.; Prospects and Challenges of Islet Regeneration as a Treatment for Diabetes: A Review of Islet Neogenesis Associated Protein; J Diabetes Sci Technol. 2007; 2:231-244.

* cited by examiner

*Primary Examiner* — Marcela M Cordero Garcia
(74) *Attorney, Agent, or Firm* — James A. Italia

(57) ABSTRACT

Embodiments of the present invention provide for novel therapies, pharmaceutical compositions and methods for insulin independence utilizing a new optimized hamster Reg3 gamma peptide, which is new to the art and has not previously been considered for development in the 30 year history since its discovery. Methods, pharmaceutical compositions and therapies novel to the prior art are utilized in this invention to render patients with recent onset and existing type 1 diabetes insulin independent by an optimized hamster Reg3 gamma peptide and an immune tolerance agent for type 1 patients to become insulin independent and used alone without an immune tolerance agent for type 2 diabetes. While not wishing to be bound by theory, optimized Reg3 gamma peptides increases beta cell generation by its demonstrated properties shown within of transforming ductal pancreatic cells into new islets.

3 Claims, No Drawings

SEQUENCE LISTING

```
<160> NUMBER OF SEQ ID NOS: 7

<210> SEQ ID NO 1
<211> LENGTH: 15
<212> TYPE: PRT
<213> ORGANISM: Mesocricetus auratus

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 2

Ile Gly Leu His Asp Pro Ser His Gly Thr Leu Pro Asn Gly Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic

<400> SEQUENCE: 3

Cys Ile Gly Leu His Asp Pro Ser His Gly Thr Leu Pro Asn Gly Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: DISULFID
<222> LOCATION: (1)..(1)
<223> OTHER INFORMATION: Homodimer formed via the creation of a
      disulfide bond between the cysteine residues of the individual
      monomers of SEQ ID NO:4.

<400> SEQUENCE: 4
```

-continued

Cys Ile Gly Leu His Asp Pro Ser His Gly Thr Leu Pro Asn Gly Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(1)
<223> OTHER INFORMATION: Homodimer formed via the creation of a
      disulfide bond between the cysteine residues of the individual
      monomers of SED ID NO:5.
<220> FEATURE:
<221> NAME/KEY: MOD_RES
<222> LOCATION: (16)..(16)
<223> OTHER INFORMATION: AMIDATION

<400> SEQUENCE: 5

Cys Ile Gly Leu His Asp Pro Ser His Gly Thr Leu Pro Asn Gly Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: N-terminal cysteine covalently bonded to a
      dimeric maleimide activated 40Kd PEG construct.

<400> SEQUENCE: 6

Cys Ile Gly Leu His Asp Pro Ser His Gly Thr Leu Pro Asn Gly Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: N-terminal cysteine covalently bonded to a
      dimeric maleimide activated 40Kd PEG construct.
<220> FEATURE:
<221> NAME/KEY: MOD_RES
<222> LOCATION: (16)..(16)
<223> OTHER INFORMATION: AMIDATION

<400> SEQUENCE: 7

Cys Ile Gly Leu His Asp Pro Ser His Gly Thr Leu Pro Asn Gly Ser
1               5                   10                  15

INSULIN INDEPENDENCE AMONG PATIENTS WITH DIABETES UTILIZING AN OPTIMIZED HAMSTER REG3 GAMMA PEPTIDE

CROSS-REFERENCE TO RELATED APPLICATIONS

This application is a divisional application of U.S. Ser. No. 14/453,414, now U.S. Pat. No. 9,321,812, filed on Aug. 6, 2014, entitled, "INSULIN INDEPENDENCE AMONG PATIENTS WITH DIABETES UTILIZING AN OPTIMIZED HAMSTER REG3 GAMMA PEPTIDE," which relies on the disclosure of and claims the benefit of priority to the filing date of U.S. Ser. No. 61/971,721, filed on Mar. 28, 2014. This application is also a continuation application of U.S. Ser. No. 14/453,421, filed on Aug. 6, 2014, which relies on the disclosure of and claims the benefit of priority to the filing date of U.S. Ser. No. 61/971,721, filed on Mar. 28, 2014. Each of the foregoing patent applications, patent publications, and patents is hereby incorporated by reference in its entirety.

REFERENCE TO SEQUENCE LISTING SUBMITTED IN COMPUTER READABLE FORM

The present application contains a Sequence Listing which has been submitted in ASCII format by way of EFS-Web and is hereby incorporated by reference herein in its entirety. The ASCII file was created Jul. 17, 2014 and named CLEV012seq.txt, which is 2.90 kilobytes in size and which is identical to the paper copy filed with this application.

FIELD OF THE INVENTION

The present invention relates to novel therapies, pharmaceutical compositions and methods for treating conditions that are associated with or are a risk factor for impaired glucose homeostasis including type 1 and 2 diabetes utilizing an optimized hamster Reg3gamma 15-amino acid peptide.

BACKGROUND OF THE INVENTION

Diabetes is one of the most serious health issues facing humanity with The World Health Organization reporting that approximately 346 million people worldwide have already been diagnosed with diabetes, making it a global challenge. Diabetes is a chronic disease that manifests when insulin production by the beta cells of the pancreas is insufficient. Type 1 and type 2 diabetes have long been considered diseases resulting from diminished insulin secretion. Research carried out over the past century has more clearly found that generating new beta cells that make insulin is the key to reversing this disease.

Beta cells, which secrete insulin, were discovered in 1869 by a medical student, Paul Langerhans. Pancreatic islets, which are predominately comprised of beta cells, are highly active metabolically, utilizing 20% of the blood supply delivered to the pancreas, but only accounting for 2% of the pancreatic mass; the remainder being extra-islet exocrine tissue containing ductal, acinar and progenitor tissue.

Among type 2 diabetes patients, there is a 50-80% reduction in beta cell mass by the time of diagnosis compared to a reduction in beta mass by 90% or more among type 1 patients, who commonly have an autoimmune component to their beta cell loss. Although the beta cell mass may expand several fold from birth to adulthood, this is not enough to compensate for the greater loss than generation of new beta cells seen in both type 1 and 2 diabetes.

Two recent NIH studies, one in children and adolescents and the other in adults demonstrate that intensive lifestyle interventions designed to improve and impact type 2 diabetes simply have no effect in children and adolescents and cannot be sustained over time among adults. The TODAY Study Group. N Engl J Med. 2012 Apr. 29. [Epub ahead of print]. Diabetes Research Program Prevention Group, Lancet. 2009; 374(9702): 1677-1686. Among children and adolescents with type 2 diabetes, therapy with metformin or lifestyle interventions did not improve diabetes control or the necessity for insulin therapy.

The TODAY study illustrates the need for new insulin-secreting beta cells to delay or prevent the adverse vascular complications of diabetes. Despite the many new treatment and technological armamentariums for diabetes, diabetes-related complications including retinopathy, blindness, neuropathy, amputations, renal insufficiency and dialysis, along with macrovascular complications including heart attack, stroke and peripheral vascular disease have risen among patients with diabetes. For example, recent studies among patients with type 1 utilizing advances including the use of glucose sensors and insulin pumps did not improve hemoglobin A1C levels as much as those seen in the DCCT trial conducted more two decades ago when there were much more limited treatment options. The DCCT Research Group. N Engl J Med. 1993; 329(14):977-986, Bergenstal R M et al, N Engl J Med. 2010; 363(4):311-320. Bergenstal R M, et al, Diabetes Care. 2011; 34(11):2403-2405.

There is a dire need to restore new beta cells and maintain beta cell mass among type 1 and type 2 diabetes. The loss of endogenous insulin is directly correlated with a multiplicity of atherogenic risk factors for microvascular and macrovascular complications. Lack of insulin, which is the hallmark of diabetes results not only in elevated glucose levels, but also results in a large number and wide complexity of metabolic abnormalities. For example, lack of insulin results in diminished activation of lipoprotein lipase resulting in increased levels of triglyceride-rich lipoproteins including chylomicrons and very low-density lipoproteins.

Among type 1 patients the pathology is more complicated, because despite known autoimmune attack on the beta cells, the delivery of agents to protect the beta cells from further attack has not rendered patients with sustained freedom from exogenous insulin. Despite dozens of clinical trials with a large variety and types of autoimmune therapies that were successful in reversing diabetes in non-obese diabetic (NOD) mice, autoimmune therapy alone provided to patients with type 1 diabetes within 3 months of their diagnosis did not sustain insulin-independence since in man, as compared to mice, there is not the significant beta cell regeneration to sustain insulin independence. Some trials with immune tolerance agents within the first months of diagnosis have rendered 67.5% of patients insulin-free within 7 weeks of therapy, yet over time, all require insulin again.

The leading hypothesis of how new beta cells can be formed in both children and adults is based upon the original works of scientists nearly a century ago who identified that in acute pancreatic injury there is new beta cell growth. Frederick Banting discovered insulin in 1921 by clamping the pancreatic ducts to induce the formation of new pancreatic cells. Dr. Banting collected the pancreatic secretions after acute pancreatic ligation and these secretions became known as insulin. Banting F G and Best C H. J Lab Clin Med. 1922; 7:464-472. This work was supported by several earlier scientists who described that although the population of beta cells is primarily formed during embryogenesis, there is the ability to grow new beta cells post-natally through a process of transformation of ductal cell tissue into insulin-producing tissue. By 1920, the regenerative powers of the pancreas were well described. Frederick Banting attributes his studies leading to the discovery of insulin on the work of Moses Barron who documented that regeneration of injured pancreatic tissue manifests from the pancreatic ducts. Barron M. Surg Gynec Obstet. 1920; 19:437-448. Prior to the widespread availability of insulin, surgeons performed partial pancreatectomies on diabetic children in the hopes of stimulating beta cell regeneration. DeTakats G. Endocrinology. 1930; 14:255-264. Benefits from these novel procedures were described, but were short-lived, likely because of ongoing autoimmune destruction.

Utilizing the data available from the Human Genome Project, this inventor and others have shown the ability to generate fully-functional pancreatic beta cells through the differentiation of non-endocrine cells. The ability of bioactive regions of the Reg gene proteins to transform extra-islet ductal tissue into islets has now been shown by more than a dozen research groups including The Section of Islet Cell and Regenerative Biology at Joslin Diabetes Center at Harvard University and The Departments of Beta Cell Regeneration at the Hagedorn Research Institute in Denmark. The Reg gene peptides identified by this inventor and others are still in development.

This inventor has previously shown that the human Reg gene peptides are directly involved in new beta cell formation from extra-islet ductal tissue. Others have confirmed the presence of Reg in the pancreas of newly diagnosed human diabetes, with subsequent data in both human ductal tissues and from BrdU studies showing that Reg serves to directly form new beta cells from extra-islet ductal tissue. Levetan C S et al, Endocr Pract. 2008; 14(9):1075-1083, Rosenberg L et al, Diabetologia. 1996; 39:256-262, Li J et al, Peptides. 2009; 30(12):2242-2249.

The 15-amino acid hamster Reg3 gamma peptide, first identified in 1983 and identified as being a hamster Reg3gamma peptide in 2007 (Brioche Biopsy's Act 2007, 1769(9-10):579-85), has not been tolerated in man due to the high quantity needed and the production of local side-effects resulting in ⅓ or more of study subjects dropping out of the clinical trials (Dungun K M et al, Diabetes Metal Res Rev. 2009; 25(6):558-565). Previously, this inventor demonstrated that a human Reg3a gene protein has successfully been administered to human pancreatic ductal tissue devoid of islets resulting in a significant increase in insulin concentrations indicating new beta cell formation; a 3-fold rise in total beta cells staining insulin in STZ-rendered diabetic mice was observed. Levetan C S., et al, Endocr Pract. 2008; 14(9):1075-1083. The human Reg3a protein and placebo-treated mice underwent an overnight fast and a fasting glucose level on the morning of day 39 of treatment. Fasting glucose levels were 258.00±84.5 mg/dl in the placebo group compared to a fasting glucose level of 111.00±11.4 mg/dL (P=0.020) in the Reg3a protein-treated mice.

Two studies by separate investigators have shown the ability of Reg peptide to transform human extra-islet pancreatic exocrine tissue into new beta cells in vitro. These studies were conducted by a methodology utilized in pancreatic islet transplantation in which the pancreatic endocrine beta cells are separated from the exocrine ductal tissue; the exocrine ductal tissue was shown to transform into new beta cells in the presence of hamster Reg3gamma peptide. Li J, et al. Peptides 2009; 30:2242-9, Assouline-Thomas B G, Diabètes 2008, 57(Suppl; 1) A2413. The current gold-standard, BrdU labeling, was used to label the beta cell lineage in rodents, which distinguishes whether new beta cells are formed by budding from pre-existing beta cells versus being formed from extra-islet ductal exocrine tissue. Kapur R, et al, Islets. 2012; 4(1).

The Section of Islet Cell and Regenerative Biology at Joslin Diabetes Center found that the 15-amino acid hamster Reg3 gamma peptide was present in the newest beta cells and islets that were formed directly from branching proliferating extra-islet ducts, which also confirms that the mechanism of action of Reg peptide is to form new beta cells from extra-islet exocrine tissue. Guo L et al, Diabetes. 2010, 59(suppl; 1) A2589. When Reg is inhibited by the administration of a blocking antibody in an animal model of pancreatic injury there was attenuated recovery, also confirming that Reg's role is both protective and regenerative during acute pancreatic injury. Viterbo D, et al. JOP. 2009; 10(1):15-23.

The Departments of Beta Cell Regeneration at the Hagedorn Research Institute and Peptide and Protein Chemistry at Novo Nordisk reported a 2-fold increase in the volume of new small islets developing from non-endocrine tissue resulting from the treatment with both the human 14 amino acid Reg3a peptide, HIP, and the 15-amino acid Reg3gamma hamster peptide Kapur R, et al, Islets. 2012; 4(1). Five days after treatment with both the 14-amino acid human Reg3a peptide, HIP, and the 15-amino acid hamster Reg3gamma peptide, INGAP, there were increased levels of new islet markers necessary for islet formation, including NGN3, NKX6.1, SOX9, and INS, indicating that REG is a catalyst for beta cell neogenesis. Kapur R, et al, Islets. 2012; 4(1). Similar to these findings, other data support that the human Reg protein and the hamster Reg3gamma peptide are an initiating factor for downstream regulation of new beta cells. Levetan C., 2010, J Diabetes; 2(2):76-84. For example, when Reg is initially expressed, PDX-1, PAX1, Ngn3, Nkx6.1, Sox9, and Ins are not expressed; once Reg is present, PDX-1, PAX1, Ngn3, Nkx6.1, Sox9 and Ins and other beta cell proliferation factors become present demonstrating that Reg activates downstream factors necessary for beta cell regeneration. Vukkadapu S S Physiol Genomics 2005:21, 201-211, Kapur R., et al., Islets. 2012; 4(1):Epub. Gun and colleagues confirmed positive Reg staining in ductal epithelium in acutely diabetic NOD mice and in the pancreas of a type 1 healthy cadaveric human pancreata or in healthy mice.

The organ specificity of the hamster Reg3 gamma protein to the pancreatic ducts has been illustrated by the tagged Reg3gamma hamster protein labeled with fluorescein isothiocyanate that was administered via intraperitoneal injection to rodents. The only organ that had fluorescent staining was the pancreas with labeling only found specifically to be within the nonendocrine pancreatic ductal populations, again confirming that the mechanism of action of Reg is transformation of extra-islet ductal cells into beta cells. Pittenger G L et al, *Diabetologia* 2009; 52 (5):735-738. There are now numerous studies confirming that the mechanism of action of the Reg peptides is to transform extra-islet exocrine ductal tissue into new islets rather than the newly formed beta cells resulting from the budding from existing beta cells.

This inventor has also investigated the role and pathways of other human hormones involved in beta cell regeneration with findings consistent with initial findings of Moore and colleagues in 1906, demonstrating the role of gastrointestinal hormones in improving diabetes control among three patients with type 1 diabetes. Levetan C. 2010, J Diabetes; 2(2):76-84, Moore et al, Biochem J. 1906; 1(1): 28-38. The mechanism of action of these gastrointestinal hormones were not only found to be in insulin secretion, but decades later these gut peptides have been shown to be involved in the transformation of extra-islet exocrine tissue into new endocrine tissue containing beta cells. Wang T C. *J Clin Invest*. 1993; 92(3):1349-56.

Not until 1999, when the use of cell lineage labeling became available, did the embryological concepts of the pancreas change. Whereas it had been thought that the pancreas was derived from both ectoderm and endoderm, it has now been shown that the entire pancreas arises only from endoderm during embryological development. This helps explain how beta progenitor cells have been described as residing diffusely throughout the adult pancreatic tissue and how growth factors transform pancreatic extra-islet ductal tissue into new beta cells. Over the past several decades, the ability to regenerate new beta cells from progenitor cells found within the pancreatic ductal tissue has been illustrated by many teams.

Despite some promise using the hamster Reg3gamma peptide in patients with type 1 diabetes with a 27% rise in stimulated c-peptide among type 1 patients with no detectable c-peptide at baseline, without 1) a tolerable agent that patients are able to use and 2) the usage of an immune tolerance agent combined with any such agent that can increase beta regeneration, an improved impact on insulin requirements is not likely to be sustained in trials (Lipsett M. Cell Biochem Biophys. 2007; 48(2-3):127-3). Data from J J Meier and colleagues demonstrates that the newest beta cells are the ones that are most vulnerable to cytokine-induced death and trigger autoimmune attack. Meier J J et al Diabetologia 2006; 49(1):83-9.

Despite early findings of patients with type 1 diabetes demonstrating a significant reduction in insulin requirements and improvements in stimulated c-peptide within 54 days of usage among type 1 patients, sustained results have not been seen and very poor tolerability with more than ⅓ of patients receiving such severe skin site reactions not to continue in the trial, further clinical development of optimized versions of the 15 amino acid hamster Reg3gamma peptide have been abandoned. This inventor discloses an optimized 15 amino acid hamster 3gamma peptide that can be further used in combination with an immune tolerance agent to protect newly formed beta cells from autoimmune destruction, for sustained insulin independence.

Some success has temporarily been seen among immune tolerance agents utilized among recent onset type 1 patients, but without new beta cell formation over time, the limited amount (fewer than 10%) of beta cells remaining at the time of type 1 diagnosis will undergo apoptosis until patients require insulin again. Clinical trials using hamster Reg3 gamma alone have concluded that 1) lack of tolerance due to injection site swelling and pain due to the large amount of peptide required 2) lack of sustained efficacy 3) lack of insulin independence have not led to consideration of new formulations of hamster Reg3 gamma that may be more tolerable in man and allowing for lower dosages.

Thus, for hamster Reg3gamma to be successful, both a new formulation that allows for more sustained action with lower amounts of drug are critical for potential success in man that has been seen in animal models. Additionally, regeneration agents alone such as with proton pump inhibitors (lansoprazole) and DPP-4 inhibitors (sitagliptin), which have shown success in mouse models do not reflect the lack of success in man among newly diagnosed type 1 patients who have shown neither long term insulin independence with a regeneration agent or an immune tolerance agent. Certain aspects of the invention, require that the optimized hamster Reg3gamma peptide be used with an immune tolerance agent among type 1 patients and to have the immune tolerance agent on board at the time that new beta cells are being generated.

The immunosuppressive drug Cyclosporine has been shown to have long-term safety and short-term efficacy for rendering new onset patients with type 1 diabetes insulin-independent. The immunosuppressive effects of Cyclosporine were discovered in 1972 in a screening test on immune suppression designed and implemented by Dr. Hartmann Stateline. The success of Cyclosporine in preventing organ rejection was later shown in kidney transplants by Calne and colleagues at the University of Cambridge and in liver transplants performed initially at the University of Pittsburgh Hospital. Cyclosporine was subsequently approved for use in 1983. Since then, it has been used to prevent and treat graft-versus-host reactions in bone marrow transplantation and to prevent rejection of kidney, heart, and liver transplantation.

In addition to transplants, Cyclosporine has also been used in psoriasis, severe atopic dermatitis, pyoderma gangrenosum, chronic autoimmune urticaria, and, infrequently, in rheumatoid arthritis and related diseases. It is commonly prescribed in the US as an ophthalmic emulsion for the treatment of dry eyes. Cyclosporine has also been used to help treat patients with acute severe ulcerative colitis that do not respond to treatment with steroids. This drug is also used as a treatment of posterior or intermediate uveitis with noninfective etiology. Cyclosporine is also currently used to experimentally treat cardiac hypertrophy.

Twenty-five years ago, Bougneres and colleagues reported in the New England Journal of Medicine that among forty children between the ages of 7 and 15 years of age with recent onset type 1 diabetes, 67.5% of patients were able to discontinue insulin within 48±5 days of initiation of 7.5 mg/kg/day of Cyclosporine in two divided dosages. Bourgneres P F. N Engl J Med 1988; 318:663-670). By 12 months after the initiation of Cyclosporine, 50% of patients remained insulin free. Over the next six years of follow-up the initial cohort was pooled with 43 more children with recent onset type 1 diabetes for a total of 83 children given Cyclosporine, who were compared to 47 children with new onset type 1 diabetes during the same time period who were not treated with Cyclosporine. DiFillippo G Diabetes 45:101-104, 1996. Over the first 4 years, the Cyclosporine-treated group kept plasma C-peptide at levels twice as high as the control group (P<0.02). It took 5.8 years for glucagon-stimulated C-peptide to become undetectable in the Cyclosporine group vs. 3.2 years in the control group. Average insulin dose remained lower by 0.2-0.4 units/kg/day. Hemoglobin A1C was lower by 1% in the Cyclosporine-treated group who also had significantly less hypoglycemia than the diabetic control subjects (P<0.05). After four years, the differences between the groups became non-significant. Other studies have found similar data that Cyclosporine had a positive impact on recent onset type 1 diabetes patients, but over time, all patients required insulin. (The Canadian-European Randomized Control Trial Group. Diabetes 1988; 37:1574-82, Assan R. Diabetes Metab Res Rev 2002; 18:464-472, Feutren G. Lancet. 1986 Jul. 19; 2(8499):119-24). In one trial of 285 patients with recent onset type 1 diabetes whom were treated for a mean of 20 months with 7.5 mg/kg/day of Cyclosporine, there were permanent renal side effects seen after following patients for 13 years. Patients in this study received renal biopsies with extensive non-invasive renal follow-up. Even patients with moderate kidney lesions on biopsy at 1 year had normal and stable clearance values at 7 to 13 years (Assan R. Diabetes Metab Res Rev 2002; 18:464-472).

Trials with Cyclosporine fell out of favor because there were no permanent remissions over time. Lack of permanent remission is hypothesized by this inventor to be due to the data suggesting that as in the case of Cyclosporine and more than a dozen other agents over the past decade utilized for protecting the beta cells from further autoimmune attack, the agents are unable to impact the remaining beta cells in the pancreas. It is estimated that fewer than 10% of functioning beta cells remain at the time of diagnosis of type 1 diabetes. Despite trials showing a positive impact of many autoimmune therapies initiated within twelve weeks of symptoms and diagnosis of type 1 diabetes, none have resulted in lasting insulin independence. Immune tolerance agents utilized among recent onset type 1 patients that in addition to Cyclosporine have shown a potential immune benefit but have not resulted in significant or sustained insulin independence include, but are not limited to the heat shock protein 60, Diapep 277, Bacille Calmette-Guérin (also known as the BCG vaccine and commonly known as the vaccine against tuberculosis), mycophenolate mofetil, daclizumab, rituximab (anti CD20), anti CD3 antibodies including hOKT3 gamma1 (Ala-Ala), and the monoclonal antibody TRX4 (ChAglyCD3), CTLA4-Ig (abatacept) a selective co-stimulation modulator as it inhibits the co-stimulation of T cells, campath-1H, anti-CD52 antibody, a humanized monoclonal antibody to T-cells, polyclonal anti-T-lymphocyte globulin (ATG), GAD antibody vaccine based on the 65 kDa isoform of the recombinant human glutamic acid decarboxylase protein (rhGAD65), diazoxide and Alpha-1 Antitrypsin.

Type 2 diabetes results from a different etiology, but similar to type 1 diabetes there is a substantial loss of 50-75% of beta cell mass at the time of diagnosis; however, the loss is not as acute as that seen from the autoimmune destruction in type 1 diabetes. The beta cell loss seen in type 2 diabetes is due to a more chronic beta cell loss that is impacted by a number of factors including lifestyle, free fatty acids and genetics. Thus, while the beta call loss is not due to sudden autoimmune destruction, there is still the need for beta cell regeneration and sustained beta cell mass.

To date, there have been no studies that combine an immune tolerance agent with a known beta cell regeneration growth factor that has been shown to directly stimulate the formation of new beta cells from ductal cells. One of the reasons that this combination of an immune tolerance agent with a Reg peptide is that it has not previously been considered and has not been obvious is because dozens of preclinical trials with rodent type 1 diabetes models including NOD mouse models have shown only the need for gastrin and other beta cell growth factors for reversal of diabetes. Likewise, rodent type 1 diabetes models including NOD mouse models have shown that using an immune tolerance agents alone is all that is needed to reverse type 1 diabetes in mice.

This inventor has shown great distinctions between the insulin-producing islets of mice and men with humans having much more complex islet structures with respect to composition of cell type, neural and vascular innervation and unique paracrine interactions that are not found in rodents. Levetan has demonstrated vast differences in the islets of mice and men, which may explain the many, many studies conducted among rodent models in the field of diabetes that later are unable to be replicated in human studies. Levetan C S et al. Endocr Pract. 2012; 27:1-36. [Epub ahead of print]. Specifically, trials with multiple different agents and types of agents have been utilized in preclinical rodent models evaluating agents that may be successful in clinical practice for usage in patients with type 1 diabetes. This inventor has also previously shown, like many other scientific teams, that after fetal development of beta cells, typically new beta cells are only derived from the existing, surviving beta cell population. Different and unique to the previous art in the field, this inventor has shown the ability to post-natally generate new beta cells by the transformation of human pancreatic ductal tissue. Levetan C. J Diabetes. 2010; 2(2):76-84, Levetan C S. Endocr Pract. 2008; 14(9):1075-83.

New and unique research by this inventor, which has not been obvious in the prior art, is 1) the ability to reverse diabetes in the diabetic mouse models may be flawed by the complexity of the human islet compared to that of the rodent and 2) the process of generating new beta cells must be from a different source than from the beta cells remaining after the diagnosis of type 1 or type 2 diabetes is made because of the limited supply (<10% for type 1 diabetes and <50-75% for type 2 diabetes). This inventor has shown the ability to transform new pools of beta cells within new islets from extra-islet ductal tissue (See U.S. Pat. Nos. 8,211,430, 7,989,415, 7,714,103 and 7,393,919).

There is a need in the art for new therapeutic modalities for the treatment of diabetes in humans that generate new beta cells from extra-islet tissue while preserving the population of nascent beta cells from destruction by the immune system.

BRIEF SUMMARY OF THE INVENTION

Embodiments of the present invention provide for novel therapies, pharmaceutical compositions and methods for insulin independence utilizing a new optimized hamster Reg3 gamma peptide, which is new to the art and has not previously been considered for development in the 30 year history since its discovery. Methods, pharmaceutical compositions and therapies novel to the prior art are utilized in this invention to render patients with recent onset and existing type 1 diabetes insulin independent by an optimized hamster Reg3 gamma peptide and an immune tolerance agent for type 1 patients to become insulin independent and used alone without an immune tolerance agent for type 2 diabetes. While not wishing to be bound by theory, optimized Reg3 gamma peptides increases beta cell generation by its demonstrated properties shown within of transforming ductal pancreatic cells into new islets. New islets contain new populations of not only beta cells generating insulin and amylin, but also, alpha cells making glucagon, delta cells making somatostatin, epsilon cells making islet ghrelin and gamma cells making pancreatic polypeptide, all of which are necessary for glucose homeostasis.

The ability to use a new Reg peptide agent that is tolerated in man to generate new islets from one's one pancreatic ductal tissue, provides a completely new approach to the treatment of diabetes. This invention identifies a new utilization of a peptide therapy, which has previously not been tolerated in man because the amount of peptide necessary to give optimal results has not been able to be given because of local side effects, which have limited its use and development over 30 years since its discovery.

This invention identifies for the first time the use of an optimized form of hamster Reg3 gamma peptide that 1) is tolerated and will not be limited in usage by local trauma due to the large dosage required 2) when combination of usage of this optimized hamster Reg3gamma peptide with an immune tolerance agent for the protection of the new beta cells provides for the potential for insulin independence among type 1 patients 3) provides therapy for the underlying cause of both type 1 and 2 diabetes by the transformation of ductal progenitor cells into new 5-celled fully functional islets 4) provides innovative therapy for type 1 and 2 diabetes and many conditions of insulin deficiency.

The therapeutic methods described in this invention are not contained within the prior art, and specifically include, but are not limited to the usage of a specific optimized 15 amino acid hamster Reg3 gamma sequence in combination with or without an immune tolerance agent, but include methods for usage in type 1 and 2 diabetes and conditions of insulin deficiency. Specifically the high dosages required of this hamster Reg3 gamma 15 amino-acid hamster peptide have resulted in severe local discomfort and swelling in the area of the subcutaneous injection limiting the success and usage of a peptide which has shown the ability to increase endogenous insulin production by 27% by day 54 in type 1 patients with no baseline c-peptide, yet, optimization of the peptide since its first clinical usage 20 years ago, has not been considered. Clinical trials have failed to develop a tolerable therapy despite clear in vitro mechanisms of action showing the formation of new beta cell formation from human pancreatic ductal tissue. The potential for this 15 amino-acid hamster Reg3 gamma peptide is enormous once it is optimized and made tolerable for usage in man. Despite its discovery in 1983, an optimized hamster Reg3 gamma peptide has never been formed, considered, invented or utilized prior, nor has an optimized hamster Reg3 gamma peptide been considered for usage with an immune tolerance agent, which this invention demonstrates is required to protect new beta cells formed by the optimized hamster Reg3 gamma peptide, from autoimmune destruction.

This invention also provides for novel therapies, pharmaceutical compositions and methods for insulin independence among type 2 diabetes patients using an optimized hamster Reg3 gamma peptide alone or in combination with other therapies as in the case of both type 1 and 2 diabetes. The development of an optimized Reg3 gamma hamster peptide has never previously been proposed or utilized in clinical trials in type 1 or two diabetes. One of the reasons that this combination of an immune tolerance agent with the hamster Reg3 gamma peptide has been considered enough in NOD trials, but this has not been the case in humans and the hamster Reg3 gamma has been so poorly tolerated that efficacious dosages have not been delivered to render patients insulin free.

Because dozens of preclinical trials with rodent type 1 diabetes models including NOD mouse models have shown only the need for gastrin and other beta cell growth factors for reversal of diabetes. Likewise, rodent type 1 diabetes models including NOD mouse models have shown that using an immune tolerance agents alone is all that is needed to reverse type 1 diabetes in mice. This inventor has shown great distinctions between the insulin-producing islets of mice and men with humans having much more complex islet structures with respect to composition of cell type, neural and vascular innervation and unique paracrine interactions that are not found in rodents.

This invention provides a new model for treatment of type 1 and 2 diabetes. Based upon the complexity and distinctions between the islets of mice and men, this invention provides for a novel therapy consisting optimization of hamster Reg3 gamma peptide with pharmaceutical compositions and methods for insulin independence and provides a methodology for treating patients requiring insulin that have not previously been described. Embodiments of the present invention provide formulations, derivatives, and modifications for the purpose of optimizing a 15 amino-acid peptide bioactive region on the hamster Reg3 gamma gene protein that has unique homology in sequence to other human Reg proteins, yet, no formulations, derivatives and modifications of this peptide have been made for it to be tolerable for usage in man. This disclosure provides specific methods for usage, including optimized versions of hamster Reg3 gamma peptides that would enable usage in man. In contrast, native hamster peptide has been found since its discovery to have too limited stability, and even when used in man in dosages that were not great enough to see significant impact on patients with diabetes, patients enrolled in clinical trials had such significant local side effects that ⅓ of patients with type 1 diabetes dropped out of clinical trials due to pain, bruising and infection to the local injection site of the hamster Reg3 gamma 15 amino acid peptide. This invention provides for a novel look at this peptide and provides for the capability of the hamster Reg3 gamma peptide to be used in man via generation of a more tolerable, stable and effective therapy that can be used for 1) the regeneration of beta cells among patients with diabetes. Methods of using this optimized hamster Reg3 gamma 15-amino acid peptide, analogs and nonpeptide peptidomemetics for treatment and reversal of type 1 diabetes and type 2 diabetes and conditions of insulin deficiency are provided.

In one embodiment, the optimized 15 amino acid hamster Reg3 gamma peptide amino Ile-Gly-Leu-His-Asp-Pro-Ser-His-Gly-Thr-Leu-Pro-Asn-Gly-Ser (SEQ ID NO: 1) and derivatives thereof are designated as agents for the treatment for 1) reversal of type 1 by enhancing beta cell replication when utilized in conjunction with an immune tolerance agent and for type 2 diabetes when utilized alone or in combination with lifestyle management and/or in combination with other diabetes agents by embodiments that allow for greater tolerability and stability in man, thus enabling the 15 amino acid hamster Reg3 gamma peptide to become a therapeutic in man for usage for the treatment of diabetes and insulin deficient states.

This peptide may also be represented by the formula: T; wherein T=SEQ ID NO:1.

In another embodiment, the 15 amino sequence hamster Reg3 gamma peptide (SEQ ID NO:1) is optimized by capping the ends. Optimization of the SEQ ID NO: 1 and to improve the Tmax and bioavailability of this peptide includes, but is not limited to blocking with an n-terminal acetyl group and a c-terminal amide group as provided below:

```
                                         (SEQ ID NO: 2)
Ac--Ile-Gly-Leu-His-Asp-Pro-Ser-His-Gly-Thr-Leu-
Pro-Asn-Gly-Ser-NH2.
```

This peptide may also be represented the formula: Ac-T-NH$_2$, where T=SEQ ID NO:1, Ac=Acetyl group, and NH$_2$=Amide group.

SEQ ID NO: 3 is the 15 amino acid hamster Reg3 gamma peptide which has an additional n-terminal cysteine residue, in purified, synthetic or recombinant form:

```
                                         (SEQ ID NO: 3)
Cys-Ile-Gly-Leu-His-Asp-Pro-Ser-His-Gly-Thr-Leu-
Pro-Asn-Gly-Ser
```

This peptide may be represented by Cys-T or U; wherein T=SEQ ID NO:1, Cys=Cysteine, and U=SEQ ID NO:3.

In another embodiment, a dimer of the peptides represented by SEQ ID NO:3 is provided as SEQ ID NO:4, in purified, synthetic, or recombinant form. The dimer forms via the creation of a disulfide bond between the cysteine residues of the individual monomers:

```
                                                (SEQ ID NO: 4)
Cys-Ile-Gly-Leu-His-Asp-Pro-Ser-His-Gly-Thr-Leu-Pro-Asn-Gly-Ser
 |
Cys-Ile-Gly-Leu-His-Asp-Pro-Ser-His-Gly-Thr-Leu-Pro-Asn-Gly-Ser.
```

This peptide may be represented by

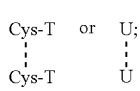

wherein T=SEQ ID NO:1, Cys=Cysteine, U=SEQ ID NO:3, and dashed line represents a disulfide bond.

In another embodiment, a dimer of the peptides represented by SEQ ID NO:3 is provided as SEQ ID NO:5, wherein each monomer has been modified to include an n-terminal cysteine residue and has been blocked with a n-terminal acetyl group and an c-terminal amide group, in purified, synthetic, or recombinant form. The dimer forms via the creation of a disulfide bond between the cysteine residues of the individual monomers:

This peptide may be represented by

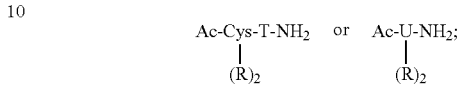

wherein R=PEG, Cys=Cysteine, T=SEQ ID NO:1, U=SEQ ID NO:3, Ac=Acetyl group, and NH$_2$=Amide group Such modifications render the sequence less susceptible to protease cleavage in serum with proteases that normally recognize free ends, thereby effectively increasing the Tmax and bioavailability of the peptides. Peptides modified in this manner demonstrate increased efficacy thereby requiring decreased dosages when administered by for example, IV, IM, SubQ or intraperitoneal routes.

```
                                                       (SEQ ID NO: 5)
Ac-Cys-Ile-Gly-Leu-His-Asp-Pro-Ser-His-Gly-Thr-Leu-Pro-Asn-Gly-Ser-NH₂
 |
Ac-Cys-Ile-Gly-Leu-His-Asp-Pro-Ser-His-Gly-Thr-Leu-Pro-Asn-Gly-Ser-NH₂.
```

This peptide may be represented by

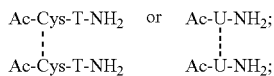

wherein T=SEQ ID NO:1, Cys=Cysteine, U=SEQ ID NO:3, Ac=Acetyl group, NH$_2$=Amide group, and dashed line represents a disulfide bond.

In another embodiment, the peptide of SEQ ID NO:2 has been covalently bonded to a dimeric maleimide activated 40 Kd PEG construct, in purified, synthetic, or recombinant form, and is provided as SEQ ID NO:6:

```
                                                (SEQ ID NO: 6)
(PEG)₂-Cys-Ile-Gly-Leu-His-Asp-Pro-Ser-His-Gly-
Thr-Leu-Pro-Asn-Gly-Ser.
```

This peptide may be represented by (R)$_2$-Cys-T or (R)$_2$-U;

wherein R=PEG, Cys=Cysteine, T=SEQ ID NO:1, and U=SEQ ID NO:3

In another embodiment, the peptide of SEQ ID NO:2 is blocked with an n-terminal acetyl group and a c-terminal amide group, and the n-terminal cysteine residue has been covalently bonded to a dimeric maleimide activated 40 Kd PEG construct, in purified, synthetic, or recombinant form, and is provided as SEQ ID NO:7:

In various embodiments, the SEQ ID NOS:1-7 may be provided alone or formulated in a pharmaceutical composition alone or in combination with an immune tolerance agent such as Cyclosporine in a pharmaceutically acceptable carrier. Furthermore, this disclosure provides additional structures beyond those described in SEQ ID NOS:1-7 such that an optimized Reg3 gamma peptide comprising any combination of addition of an N-terminal cysteine, acetylation at the N-terminus, amidated at the C-terminus, and/or PEGylated at either terminus, in monomeric or dimeric form, is provided. These additional structures may be provided alone or formulated in a pharmaceutical composition alone or in combination with an immune tolerance agent such as Cyclosporine in a pharmaceutically acceptable carrier.

An exemplary embodiment provides a pharmaceutical composition comprising a peptide comprising SEQ ID NO:1 and an immune tolerance agent such as Cyclosporine.

Another exemplary embodiment comprises an optimized Reg3 gamma peptide comprising the sequence of SEQ ID NO:1 that is acetylated at the N-terminus, amidated at the C-terminus, and/or PEGylated at either terminus. The optimized Reg 3 gamma may have the N-terminus or C-terminus covalently bonded to a dimeric maleimide activated 40 Kd PEG construct. The optimized Reg3 gamma peptide may be provided alone or formulated in a composition alone or in combination with an immune tolerance agent such as Cyclosporine in a pharmaceutically acceptable carrier.

Another exemplary embodiment comprises an optimized Reg 3 gamma peptide comprising the sequence of SEQ ID

```
                                                       (SEQ ID NO: 7)
Ac-Cys-Ile-Gly-Leu-His-Asp-Pro-Ser-His-Gly-Thr-Leu-Pro-Asn-Gly-Ser-NH₂
 |
(PEG)₂.
```

NO:3 that is acetylated at the N-terminus, amidated at the C-terminus, and/or PEGylated at either terminus. The optimized Reg 3 gamma peptide may have the N-terminus or C-terminus covalently bonded to a dimeric maleimide activated 40 Kd PEG construct. The optimized Reg3 gamma peptide may be provided alone or formulated in a composition alone or in combination with an immune tolerance agent such as Cyclosporine in a pharmaceutically acceptable carrier.

Another exemplary embodiment comprises an optimized Reg 3 gamma peptide which is an isolated peptide homodimer, wherein each molecule consists of the amino acid sequence of SEQ ID NO:3 and the homodimer is obtained by dimerization through the free cysteine in the two molecules of the dimer. The optimized Reg 3 gamma peptide homodimer may be acetylated at the N-terminus, amidated at the C-terminus, and/or PEGylated at either terminus. The optimized Reg3 gamma peptide may have the N-terminus or C-terminus covalently bonded to a dimeric maleimide activated 40 Kd PEG construct. The optimized Reg3 gamma peptide homodimer may be provided alone or formulated in a composition alone or in combination with an immune tolerance agent such as Cyclosporine in a pharmaceutically acceptable carrier.

Another exemplary embodiment comprises a method of treating type 1 or type 2 diabetes, comprising administering to a subject a therapeutically effective amount of a pharmaceutical composition comprising a peptide comprising SEQ ID NO:1 and an immune tolerance agent such as Cyclosporine.

Another exemplary embodiment comprises a method of treating type 1 or type 2 diabetes, comprising administering to a subject a therapeutically effective amount of a pharmaceutical composition comprising any optimized Reg3 gamma peptide of this disclosure alone or in combination with an immune tolerance agent such as Cyclosporine.

DETAILED DESCRIPTION OF EXEMPLARY EMBODIMENTS OF THE INVENTION

All references listed in this specification, including books, journal articles, published patent applications, and issued patents, are hereby incorporated by reference in their entirety.

To date, over the past thirty years, the hamster Reg3 gamma peptide has not been able to be utilized by patients with diabetes due to poor stability and tolerability in man, despite the safe and efficacious preclinical and early clinical results from decades ago. Throughout the history of the 15 amino acid hamster Reg3gamma peptide and its introduction to human patients with type 1 and 2 diabetes, it has not been developed nor have there been any changes in formulation to make it a potential therapeutic among patients with diabetes.

In one embodiment, derivatives of hamster Reg3 gamma peptide are created by blocking the peptide with an N-terminal acetyl group and a C-terminal amide group to form the peptide of SEQ ID NO: 2. In another embodiment, derivatives of hamster Reg3 gamma peptide are created by adding a cysteine residue to the n-terminal of SEQ ID NO: 1 to form Hamster Reg3 gamma Cys (SEQ ID NO: 3) which results in a compound which is capable of forming dimers in solution to form HamsterReg3 gamma CysDimer (SEQ ID NO: 4). Such a modification increases the stability hamster Reg3gamma Cys variants by avoiding proteases which recognize hamster Reg3gamma Cys or hamster Reg3gamma Cys variants in monomer form.

In another embodiment, hamster Reg3 gamma Cys variants are blocked with an N-terminal acetyl group and a C-terminal amide group. Such modifications render the sequence less susceptible to protease cleavage in serum with proteases that normally recognize free ends and resulting in a compound which is capable of forming dimers in solution hamster Reg3 gamma Cys Blocked Dimer (SEQ ID NO: 5), thereby increasing the stability of hamster Reg3 gamma peptide Cys Blocked variants by avoiding proteases which recognize hamster Reg3 gamma or Hamster Reg3 gamma peptide Cys Blocked variants in monomer form.

In another embodiment, hamster Reg 3gamma peptide Cys variants are modified by covalently binding a dimeric maleimide activated 40 Kd PEG construct to the n-terminal cysteine residue hamster Reg3 gamma peptide CysPEG (SEQ ID NO: 6). Such a modification improves the stability of hamster Reg3gammaCys in serum resulting in increased bioavailability and dosing efficacy of hamster Reg3gamma are variants in therapeutic strategies for beta cell replication for reversing diabetes in vivo.

In another embodiment, hamster Reg3 gamma Cys-Blocked variants are modified by covalently binding a dimeric maleimide activated 40 Kd PEG construct (Hamster Reg3gamma peptide CysBlockedPEG (SEQ ID NO: 7). Such a modification improves the stability hamsterReg3 gamma CysBlocked variants in serum resulting in increased bioavailability and dosing efficacy of hamster Reg3gamma peptide CysBlocked variants in therapeutic strategies for stimulating islet neogenesis and reversing diabetes in vivo.

In another embodiment, a hamster Reg3 gamma peptide analogs and hamster Reg3 gamma peptidomemetics are designed to improve the efficacy and therapeutic ability for beta cell replication for improving and reversing diabetes in vivo.

Further embodiments of the present invention provide methods for administering the optimized hamster Reg3gamma peptide compounds (SEQ ID NOs: 1-7) alone or in combination with other therapeutic agents for stimulating pancreatic islet cell regeneration. In various embodiments, the methods of the invention can be practiced by administration of a therapeutically effective amount of optimized hamster Reg3 gamma peptide alone, in combination with insulin, in combination with insulin and another agent, and in combination with one or more agents other than insulin.

The peptides may be produced through recombinant molecular biology techniques or solid phase synthesis techniques. Recombinant molecular biology techniques include those described in Molecular Cloning: A Laboratory Manual, Green and Sanbrook, 2012. Solid-phase synthesis techniques are described in Merrifield, in J. Am. Chem. Soc., 15:2149-2154 (1963), M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985); as well as other reference works known to those skilled in the art such. A summary of peptide synthesis techniques may be found in J. Stuart and J. D. Young, Solid Phase Peptide Synthelia, Pierce Chemical Company, Rockford, Ill. (1984), which is incorporated herein by reference. The synthesis of peptides by solution methods may also be used, as described in The Proteins, Vol. II, 3d Ed., p. 105-237, Neurath, H. et al., Eds., Academic Press, New York, N.Y. (1976). Appropriate protective groups for use in such syntheses will be found in the above texts, as well as in J. F. W. McOmie, Protective Groups in Organic Chemistry, Plenum Press, New York, N.Y. (1973), which is incorporated herein by reference. In general, these synthetic methods involve the sequential addition of one or more amino acid residues or protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine. Block synthesis techniques may also be applied to both the solid phase and solution methods of peptide synthesis. Rather than sequential addition of single amino acid residues, preformed blocks comprising two or more amino acid residues in sequence are used as either starting subunits or subsequently added units rather than single amino acid residues. Alternative or additional peptide synthesis methods and techniques can be found in Peptide Chemistry: A Practical Textbook: 2nd Edition, Miklos Bodanszky, 1993.

Proteins having the amino acid sequence of SEQ ID NOS:1-7 thereof or a portion thereof may also be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support, i.e., polystyrene beads. The proteins are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile. Details of appropriate chemistries, resins, protecting groups, protected amino acids and reagents are well known in the art and so are not discussed in detail herein (See, Atherton et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting optimized is accomplished using conventional procedures, such as preparative HPLC using gel permeation, partition and/or ion exchange chromatography. The choice of appropriate matrices and buffers are well known in the art and so are not described in detail herein.

Protocols for blocking peptides with acetyl and amide groups are known in the art and can be found in a number of protein protocol textbooks known in the art. Specific examples include those published in Methods in Molecular Biology, Vol. 35: Peptide Synthesis Protocols, Chapter 8: Site-Specific Chemical Modification Procedures, Edited by M W Pennington and B M Dunn, 1994, as well as U.S. Pat. No. 4,708,934, U.S. Pat. No. 5,503,989, U.S. Patent Application Publication No. US 20060127995. Alternative or additional blocking procedures can be found in Peptide Chemistry: A Practical Textbook: 2nd Edition, Miklos Bodanszky, 1993.

Inert polymer molecules such as high molecular weight polyethyleneglycol (PEG) can be attached to a peptide of this disclosure or an analog or derivative thereof with or without a multifunctional linker either through site-specific conjugation of the PEG to the N- or C-terminus of the protein or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules. Unreacted PEG can be separated from peptide-PEG conjugates by size-exclusion or by ion-exchange chromatography.

The optimized peptides may also be PEGylated at cysteine residues through maleimide chemistry. Maleimide-activated PEG reacts with the thiols of cysteine residues of protein and to form stable thioether linkages and are highly stable against hydrolysis. The maleimide moiety reacts rapidly with the thiol group without hydrolysis around neutral pH. Protocols for creating maleimide-activated PEG constructs may be found in Schumacher et al., In Situ Maleimide Bridging of Disulfides and a New Approach to Protein PEGylation, Bioconjugate Chem., 2011, 22 (2), pp 132-136, Doherty et al., Site-Specific PEGylation of Engineered Cysteine Analogs of Recombinant Human Granulocyte-Macrophage Colony-Stimulating Factor, Bioconjug Chem. 2005; 16(5): 1291-1298, US Patent Application Publication No. 20090298746 A1, European Patent No. EP 1881850 B1, European Patent No. EP 2178900 B1.

Other embodiments of the present invention provide pharmaceutical formulations and unit dose forms of optimized hamster Reg3gamma peptide. In one embodiment, the pharmaceutical formulation provided contains optimized hamster Reg3 gamma peptide alone or in combination with one or more other active pharmaceutical ingredients (APIs). In one embodiment, the API is an or agents in soluble liposome preparations that allow the optimized hamster Reg3gamma peptide to be administered by a variety of routes, including subcutaneously, intramuscularly, intravenously, and even orally, depending on the formulation selected. In one embodiment, the formulation is for general systemic administration, but in other embodiments, the formulation comprises a targeting agent for targeted administration to specific locations, receptors, cells, tissues, organs, or organ systems within a subject.

Provided is a composition comprising one or more of the herein provided optimized peptides in a pharmaceutically acceptable carrier. Thus, provided is a composition comprising one or more any of the herein provided optimized peptides in a pharmaceutically acceptable carrier. Further, provided are compositions comprising one or more optimized peptides with an immune tolerance agent.

For example, provided is a composition comprising the peptide of SEQ ID NO:1 and in a pharmaceutically acceptable carrier. Another example is a composition comprising the peptide of SEQ ID NO: 1 and Cyclosporine A in a pharmaceutically acceptable carrier. Another example is a composition comprising the peptide of SEQ ID NO: 2 in a pharmaceutically acceptable carrier. Another example is a composition comprising the peptide of SEQ ID NO: 2 and Cyclosporine in a pharmaceutically acceptable carrier. Another example is a composition comprising a peptide of SEQ ID NO: 3 in a pharmaceutically acceptable carrier. Another example is a composition comprising the peptide of SEQ ID NO: 3 and Cyclosporine in a pharmaceutically acceptable carrier. Another example is a composition comprising a peptide of SEQ ID NO: 4 in a pharmaceutically acceptable carrier. Another example is a composition comprising the peptide of SEQ ID NO:4 and Cyclosporine in a pharmaceutically acceptable carrier. Another example is a composition comprising a peptide of SEQ ID NO: 5 in a pharmaceutically acceptable carrier. Another example is a composition comprising the peptide of SEQ ID NO: 5 and Cyclosporine in a pharmaceutically acceptable carrier. Another example is a composition comprising a peptide of SEQ ID NO:6 in a pharmaceutically acceptable carrier. Another example is a composition comprising the peptide of SEQ ID NO:6 and Cyclosporine in a pharmaceutically acceptable carrier. Another example is a composition comprising a peptide of SEQ ID NO:7 in a pharmaceutically acceptable carrier. Another example is a composition comprising the peptide of SEQ ID NO:7 and Cyclosporine in a pharmaceutically acceptable carrier.

By "pharmaceutically acceptable" is meant a material that is not biologically or otherwise undesirable, i.e., the material may be administered to a subject, along with the optimized peptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered topically, orally, or parenterally. For example, the compositions can be administered extracorporeally, intracranially, intravaginally, intraanally, subcutaneously, intradermally, intracardiac, intragastric, intravenously, intramuscularly, by intraperitoneal injection, transdermally, intranasally, or by inhalation. As used herein, "intracranial administration" means the direct delivery of substances to the brain including, for example, intrathecal, intracisternal, intraventricular or transsphenoidal delivery via catheter or needle.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

As used herein, "topical intranasal administration" means delivery of the compositions into the nose and nasal passages through one or both of the nares and can comprise delivery by a spraying mechanism or droplet mechanism, or through aerosolization of the optimized peptide(s). Administration of the compositions by inhalant can be through the nose or mouth via delivery by a spraying or droplet mechanism. Delivery can also be directly to any area of the respiratory system (e.g., lungs) via intubation.

The exact amount of the compositions required will vary from subject to subject, depending on the species, age, weight and general condition of the subject, the severity of the condition being treated, the particular optimized peptide used, its mode of administration and the like. Thus, it is not possible to specify an exact amount for every composition. However, an appropriate amount can be determined by one of ordinary skill in the art using only routine experimentation given the teachings herein.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8, from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, gels (e.g., poloxamer gel), drops, controlled-release compositions, timed release compositions, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), glasses, nanosphere, aerosol, lotion, cream, fabric, plastic, tissue engineered scaffold, matrix material, tablet, implanted container, powder, oil, resin, wound dressing, bead, microbead, slow-release compounds, timed-release compounds, capsule, injectables, intravenous drips, pump device, silicone implants, or any bio-engineered materials.

Compositions for oral administration include powders or granules, suspensions or solutions in water or non-aqueous media, capsules, sachets, or tablets. Thickeners, flavorings, diluents, emulsifiers, dispersing aids or binders may be desirable. Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Slow dissolving polymers such as poly(bis(p-carboxyphenoxy)-propane:sebacic acid—CCP:SA) may also be used to generate wafers or beads that control or time the release of the composition. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the peptides of this disclosure are dissolved or suspended in suitable liquids, such as fatty oils, or liquid paraffin, optionally with stabilizers.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Fatty oils may comprise mono-, di- or triglycerides. Mono-, di- and triglycerides include those that are derived from C6, C8, C10, C12, C14, C16, C18, C20 and C22 acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

Suitable formulations for parenteral administration include aqueous solutions of hamster Reg3 gamma and optimized hamster Reg3 gamma peptides and optionally immune tolerance agents in water-soluble form, for example, water-soluble salts and alkaline solutions. In addition, suspensions of hamster Reg3 gamma and optimized hamster Reg3 gamma peptides and optionally immune tolerance agent(s) as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions may be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which hamster Reg3 gamma and optimized hamster Reg3 gamma peptides and optionally immune tolerance agents, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of hamster Reg3 gamma immune or optimized hamster Reg3 gamma peptides in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the hamster Reg3 gamma, and optimized hamster Reg3 gamma peptides and optionally immune tolerance agent(s) in a suitable high molecular weight alcohol such as propylene glycol or polyethylene glycol.

Suitable routes of administering the pharmaceutical preparations include oral, rectal, topical (including dermal, buccal and sublingual), vaginal, parenteral (including subcutaneous, intramuscular, intravenous, intradermal, intrathecal, intratumoral, and epidural) and by naso-gastric tube. It will be understood by those skilled in the art that the preferred route of administration will depend upon the condition being treated and may vary with factors such as the condition of the recipient.

Possible pharmaceutical preparations which can be used rectally include, for example, suppositories, which consist of a combination of one or more of the peptides of this disclosure with a suppository base. Suitable suppository bases are, for example, natural or synthetic triglycerides, or paraffin hydrocarbons. In addition, it is also possible to use gelatin rectal capsules which consist of the peptides of this disclosure with a base. Possible base materials include, for example, liquid triglycerides, polyethylene glycols, or paraffin hydrocarbons.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of any counter indications. Dosage can vary, and can be administered in one or more dose administrations daily, for one or several days. Guidance can be found in the literature for appropriate dosages for given classes of pharmaceutical products. The range of dosage largely depends on the application of the compositions herein, severity of condition, and its route of administration.

For example, in applications as a laboratory tool for research, the optimized peptide compositions can be used in doses as low as 0.01% w/v. Significantly higher concentrations of the compositions by themselves or in combination with other compounds may be used in applications like cancer/tumor therapy. Thus, upper limits of the provided polypeptides may be up to 2-5% w/v or v/v if given as an initial bolus delivered. Recommended upper limits of dosage for parenteral routes of administration for example intramuscular, intracerebral, intracardicardiac and intraspinal could be up to 1% w/v or v/v depending on the severity of the disease. This upper dosage limit may vary by formulation, depending for example on how the polypeptide(s) is combined with other agents promoting its action or acting in concert with the polypeptide(s).

For continuous delivery of the provided polypeptides, for example, in combination with an intravenous drip, upper limits of 0.01 g/Kg body weight over time courses determined by the doctor based on improvement in the condition can be used. In another example, upper limits of concentration of the provided nucleic acids delivered internally for example, intramuscular, intracerebral, intracardicardiac and intraspinal would be 50-100 µg/ml of solution. Again, the frequency would be determined by the Doctor based on improvement.

The optimized peptides of this disclosure may be optionally formulated with an immune tolerance agent. The immune tolerance agent may be present at a concentration of 0.01% to 10% w/v, depending on which immune tolerance agent is used and the type of vehicle. In one embodiment, the immune tolerance agent is Cyclosporine. For example, Cyclosporine may be present in a concentration of 1 mg/ml to 200 mg/ml. The optimized peptides of this disclosure may be formulated with an immune tolerance agent using any vehicle described herein.

In other embodiments of the present invention, provided are methods of treating a pathology associated with impaired pancreatic function in a subject in need of such treatment. The method may comprise the step of administering one or more agents for stimulating pancreatic islet cell regeneration in addition to the optimized hamster Reg3gamma peptide. In one aspect of this embodiment, the agents are selected from hamster Reg3 gamma or hamster Reg3 gamma-related peptides other than Optimized Reg3 gamma, amylin/Pramlintide (SYMLIN™), exendin-4 (EXENATIDE™), GIP, GLP-1, GLP-1 receptor agonists, GLP-1 analogs, hamster INGAP peptide and related peptides, Liraglutide (NN2211), and a dipeptidyl peptidase inhibitor, which blocks the degradation of GLP-1.

In another embodiment, methods of treating a pathology associated with impaired pancreatic function in a subject in need of such treatment are provided. The method may comprises one or more of the steps of (1) intensifying glycemic control; (2) administering oral vitamin D3 (cholecalciferol) to maintain 25-hydroxyvitamin levels above 40 ng/ml; (3) administering one or more immune therapies for protecting new islet cell formation, including administration of immunosuppressive agents; (4) administering selenium 5) administering Optimized hamster Reg3gamma peptide in combination with insulin but decreasing the insulin administered over time; and (5) repeatedly administering a therapy for protection of islets, preferably on a 3 to 24 month basis, depending on the selected immune therapy, in addition to the step of administering optimized hamster Reg3gamma peptide.

In another embodiment, methods of treating a pathology associated with impaired pancreatic function in a subject in need of such treatment are provided. The method may comprise one or more of the steps of: (1) intensifying glycemic control; (2) administering oral vitamin D3 (cholecalciferol) to maintain 25-hydroxyvitamin levels above 40 ng/ml; (3) administering an agent for stimulating pancreatic islet regeneration in addition to Optimized hamster Reg gamma peptide, including but not limited to the 15 amino-acid hamster Reg3 gamma peptide and 15 amino acid hamster Reg gamma analogs other than Optimized hamster Reg3 gamma peptide; (4) co-administering an agent selected from the group consisting of amylin/Pramlintide (SYMLIN™), exendin-4 (EXENATIDE™; BYETTA™), Gastrin, Epidermal Growth Factor and Epidermal Growth Factor analog GIP, GLP-1, GLP-1 receptor agonists, GLP-1 analogs, INGAP, Liraglutide (NN2211), and a dipeptidyl peptidase IV inhibitor, which blocks the degradation of GLP-1; and (5) reducing, or tapering off, administration of another diabetes therapy.

In another embodiment, methods of treating a pathology associated with impaired pancreatic function in a subject in need of such treatment are provided. The method may comprise in addition to administering the optimized 15 amino acid hamster Reg3gamma peptide, the step of administering one or more agents that inhibit, block, or destroy the autoimmune cells that target pancreatic islets. Such therapies are termed "immune therapies" above. In various aspects of this embodiment, the agents that inhibit, block, or destroy the autoimmune cells that target pancreatic islets are selected from the group consisting of Cyclosporine A, Anti CD-3 antibodies including hOKT3γ1(Ala-Ala) and ChAglyCD3 that target the immune response and specifically block the T-lymphocytes that cause beta cell death in type 1 diabetes; Sirolimus (Rapamycin); Tacrolimus (FK506); a heat-shock protein 60 (Diapep277); an anti-Glutamic Acid Decarboxylase 65 (GAD65) vaccine; Mycophenolate Mofetil alone or in combination with Daclizumab; the anti-CD20 agent, Rituximab; Campath-1H (Anti-CD52 Antibody), lysofylline; antithymocyte globulin (ATG), Vitamin D; IBC-VSO vaccine, which is a synthetic, metabolically inactive form of insulin designed to prevent pancreatic beta-cell destruction; interferon-alpha; and a vaccine using $CD4^+CD25^+$ antigen-specific regulatory T cells. These or similar agents can be used in the combination therapies provided by the invention that utilize regulatory T cells either directly or through the use of immunotherapy to arrest the destruction of insulin-producing cells.

In another embodiment of the present invention, methods of treating a pathology associated with impaired pancreatic function in a subject in need of such treatment, wherein at least one symptom of the pathology associated with impaired pancreatic function is treated or reduced as a result of the administration of the optimized 15 amino-acid hamster Reg3 gamma peptide are provided. In one aspect of this embodiment, the symptom is selected from low levels of insulin or insulin activity, insulin resistance, hyperglycemia, hemoglobin A1C level greater than 6.0%, frequent urination, excessive thirst, extreme hunger, unusual weight loss or gain, being overweight, increased fatigue, irritability, blurry vision, genital itching, odd aches and pains, dry mouth, dry or itchy skin, impotence, vaginal yeast infections, poor healing of cuts and scrapes, excessive or unusual infections, loss or worsening of glycemic control, fluctuations in blood glucose, fluctuations in blood glucagon, and fluctuations in blood triglycerides, with hyperglycemia ultimately leading to microvascular and macrovascular complications, which include visual symptoms that lead to blindness, accelerated kidney impairment that can lead to renal failure necessitating dialysis and kidney transplant and neuropathy leading to foot ulcers and amputations. Additionally, recent studies have demonstrated both microvascular and macrovascular/cardiovascular risk reduction among type 1 diabetes patients who have improved glycemic control.

In another embodiment, methods of treating a pathology associated with impaired pancreatic function in a subject in need of such treatment are provided. The pathology associated with impaired pancreatic function is any one of type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome/dysmetabolic syndrome, being overweight, obesity, hyperlipidemia, hypertriglyceridemia, eating disorders, anovulatory cycles and polycystic ovarian syndrome.

Embodiments of the invention also provide antibodies which selectively bind to the optimized 15 amino acid Reg3 gamma peptide. In one embodiment, the antibody is a monoclonal antibody. In another embodiment, the antibody is a polyclonal antibody. Such antibodies can be used in diagnostic methods provided by the invention, which methods comprise detecting the optimized 15 amino acid hamster Reg3gamma peptide levels in the serum or tissue of a mammal. In one embodiment the diagnostic method is used to monitor treatment with the optimized 15 amino acid Reg3 hamster gamma peptide to ensure that therapeutically effective levels are being achieved in a patient receiving such therapy.

Embodiments of the invention also provide kits for treating a patient having type 1 or type 2 diabetes or other condition in which there are aberrant insulin levels, perturbation in glucose metabolism or insulin resistance, comprising a therapeutically effective dose of the 15 amino acid optimized hamster Reg 3 gamma peptide and optionally at least one agent for stimulating GLP-1 receptors or enhancing GLP-1 levels, promoting beta cell regeneration, increased satiety, decreased food intake and weight loss, either in the same or separate packaging, and instructions for its use. Further embodiments provide a kit for measuring optimized hamster Reg3 gamma levels in a sample, the kit comprising an optimized hamster Reg3 gamma-specific antibody and optionally optimized hamster Reg3 gamma and optionally a labeling means.

Embodiments of the present invention provide detailed strategies for optimizing the stability and solubility of a 15 amino-acid hamster Reg3 gamma for improved use as a therapeutic agent and are a peptide fragment of the hamster protein regenerating islet-derived 3 gamma protein. Embodiments of the invention also provide pharmaceutical compositions and therapies for the treatment of pancreatic dysfunction, including type 1 and type 2 diabetes, with such compositions. In one embodiment, these compositions comprise an optimized 15 amino acid hamster Reg 3 gamma. In another embodiment, these compositions include optimized hamster Reg3 gamma and other agents that affect glucose metabolism. Included among these other agents are agents that are involved in pancreatic islet neogenesis and agents that inhibit, block, or destroy the autoimmune cells that target pancreatic islet cells. In one embodiment, the therapies of the invention are practiced by administering a therapeutically effective dose of the hamster optimized Reg3 gamma peptide to a mammal in need of such therapy. In another embodiment, the therapies of the invention are practiced by administering a therapeutically effective dose of the hamster optimized Reg 3 gamma peptide to a mammal in need of such therapy in combination with another agent (such as a hormone or compound) that affects glucose metabolism, including but not limited to hormones or compounds that are involved in beta cell regeneration, satiety, and gastric emptying, such as GLP-1, GIP, GLP-1 receptor analogs, GLP-1 analogs, and Dipeptidyl Peptidase-4 Inhibitors, which prevent destruction of GLP-1, and agents that inhibit, block, or destroy the autoimmune cells that target pancreatic cells. In this latter embodiment, the Optimized hamster Reg3 gamma and the other agent may be administered separately or may first be admixed to provide a combination composition of the invention and administered simultaneously.

An exemplary composition comprises 100 mg optimized Blocked Reg3 gamma peptide (SEQ ID NO:2) in a vial for intravenous injection. The vial contains inactive ingredients including mannitol (600 mg), L-threonine (160 mg), polysorbate 80 (120 mg), sodium citrate dihydrate (235 mg), and hydrochloric acid (160 mg). When reconstituted with 41 mL Sterile Water for Injection, the resulting solution will contain 2.5 mg/ml optimized Reg3 gamma peptide (SEQ ID NO:2).

Another exemplary composition comprises 250 mg optimized Cys N-terminal Reg3 gamma peptide (SEQ ID NO:3) in 100 mL of Lactated Ringers to provide a solution of 2.5 mg/ml optimized Reg3 gamma peptide (SEQ ID NO:3).

Another exemplary composition comprises 200 mg optimized Cys Dimer Reg3 gamma peptide (SEQ ID NO:4) in 100 mL of 5% dextrose in 0.9% sodium chloride to provide a solution of 2.0 mg/ml optimized Reg3 gamma peptide (SEQ ID NO:4).

Another exemplary composition comprises 500 mg optimized Cys Blocked Dimer Reg3 gamma peptide (SEQ ID NO:5) in 1000 ml in 0.9% sodium chloride to provide a solution of 0.5 mg/ml optimized Reg3 gamma peptide (SEQ ID NO:5).

Another exemplary composition comprises 100 mg optimized Cys PEG Reg3 gamma peptide (SEQ ID NO:6) in 1 ml MIGLYOL 810 enclosed in a gelatin capsule.

Another exemplary composition comprises 100 mg optimized Cys Blocked PEG Reg3 gamma peptide (SEQ ID NO:7) in 1 ml LABRAFAC CC enclosed in a gelatin capsule.

In another embodiment, the invention provides a combination product comprising at least one optimized Reg3 gamma peptide combined with an immune tolerance agent. The combination product may be used in type 1 and 2 diabetes, PreDiabetes or diseases of insulin deficiency, beta cell deficiency, insulin resistance and impaired glucose metabolism. One exemplary composition comprises 100 mg Reg3 gamma peptide (SEQ ID NO:1) and 5 g Cyclosporine in 50 ml distilled water to provide a solution of 2 mg/ml Reg3 gamma peptide (SEQ ID NO:1) and 100 mg/ml Cyclosporine.

Another exemplary composition comprises 100 mg Reg3 gamma peptide (SEQ ID NO:1) and 5 g Cyclosporine in 50 ml 0.9% NaCl; to provide a solution of 2 mg/ml Reg3 gamma peptide (SEQ ID NO:1) and 100 mg/ml Cyclosporine.

Another exemplary composition comprises 150 mg optimized Blocked Reg3 gamma peptide (SEQ ID NO:2) and 5 g Cyclosporine in 50 ml 0.9% NaCl to provide a solution of 3 mg/ml optimized Reg 3 gamma peptide (SEQ ID NO:2) and 100 mg/ml Cyclosporine.

Another exemplary composition comprises 200 mg optimized Cys Reg3 gamma peptide (SEQ ID NO:3) and 5 g Cyclosporine in 50 ml 0.9% NaCl to provide a solution of 4 mg/ml optimized Reg 3 gamma peptide (SEQ ID NO:3) and 100 mg/ml Cyclosporine.

Another exemplary pharmaceutical composition comprises 250 mg CysDimer Reg3 gamma peptide (SEQ ID NO:4) and 5 g Cyclosporine in 50 ml 0.9% NaCl to provide a solution of 5 mg/ml optimized Reg 3 gamma peptide (SEQ ID NO:4) and 100 mg/ml Cyclosporine.

Another exemplary pharmaceutical composition comprises 150 mg CysBlocked Dimer Reg3 gamma peptide (SEQ ID NO:5) and 5 g Cyclosporine in 50 ml Lactated Ringer's to provide a solution of 3 mg/ml optimized Reg 3 gamma peptide (SEQ ID NO:5) and 100 mg/ml Cyclosporine.

Another exemplary pharmaceutical composition comprises 200 mg CysPEG Reg3 gamma peptide (SEQ ID NO:6) and 5 g Cyclosporine in 50 ml 0.9% Lactated Ringer's to provide a solution of 4 mg/ml optimized Reg 3 gamma peptide (SEQ ID NO:6) and 100 mg/ml Cyclosporine.

Another exemplary pharmaceutical composition comprises 250 mg CysBlockedPEG Reg3 gamma peptide (SEQ ID NO:7) and 5 g Cyclosporine in 50 ml Lactated Ringer's to provide a solution of 5 mg/ml optimized Reg 3 gamma peptide (SEQ ID NO:7) and 100 mg/ml Cyclosporine.

Another exemplary pharmaceutical composition of the present invention comprises 60 mg Reg3 gamma peptide (SEQ ID NO:1) and 100 mg Cyclosporine enclosed in a hard gelatin capsule with lactose as a filler.

Another exemplary pharmaceutical composition of the present invention comprises 50 mg Blocked Reg3 gamma peptide (SEQ ID NO:2), 100 mg Cyclosporine, QS to 1 ml the pharmaceutically acceptable carrier LABRASOL (Gattefosse S A), which is PEG-8 caprylic/capric glycerides, enclosed in a soft gelatin capsule.

Another exemplary pharmaceutical composition of the present invention comprises 100 mg N-terminal Cys Reg3 gamma peptide (SEQ ID NO:3), 50 mg Cyclosporine, QS to 1 ml the pharmaceutically acceptable carrier Miglyol 812N (medium chain triglycerides), enclosed in a hard gelatin capsule.

Another exemplary pharmaceutical composition of the present invention comprises 75 mg CysDimer Reg3 gamma peptide (SEQ ID NO:4), 100 mg Cyclosporine, and alcohol, USP, absolute, 12.7% v/v, enclosed in a soft gelatin capsule.

Another exemplary pharmaceutical composition is an oral solution wherein each ml contains 50 mg CysBlockedDimer Reg3 gamma peptide (SEQ ID NO:5), 100 mg Cyclosporine, alcohol, Ph. Helv. 12.5% by volume dissolved in an olive oil, Ph. Helv./Labrafil M 1944 CS (polyoxyethylated oleic glycerides) vehicle which must be further diluted with milk, chocolate milk, or orange juice before oral administration.

Another exemplary pharmaceutical composition is an oral suspension wherein each ml contains 3 mg CysPEG Reg3 gamma peptide (SEQ ID NO:6) and 5 mg Cyclosporine, QS to 1 ml 8.4% sodium bicarbonate (aqueous solution).

Another exemplary composition is 30 mg CysBlockedPEG Reg3 gamma peptide (SEQ ID NO:7) and 50 mg Cyclosporine formulated in a pill comprising pharmaceutically acceptable carriers such as fillers (e.g. saccharides, cellulose preparations and/or calcium phosphates).

Another exemplary pharmaceutical composition of the present invention comprises 50 mg human Reg3 gamma peptide (SEQ ID NO:1), 100 mg Cyclosporine, and alcohol, USP, absolute, 12.8% v/v, enclosed in a soft gelatin capsule.

EXAMPLE 1

The Optimized Hamster Reg3 Gamma Peptide Used with Cyclosporine for Insulin Independence Among Type 1 Diabetes Patients The combination of an immune tolerance agent (e.g. Cyclosporine initially dosed at 7.5 mg/kg/day in divided dosages at breakfast and dinner and based on peak and trough levels, the dosage will be modified to optimize immune tolerance and limit side effects) with optimized hamster Reg3gamma (each of SEQ ID NOS:2-7) dosed at 30 mg per day given in two divided given subcutaneously (15 mg per dosage) for children less than 11 years old weighing 66 pounds or less. For children older than 11 years and weighing more than 66 pounds optimized hamster Reg3gamma (each of SEQ ID NOS:2-7) will be dosed as 60 mg per day given subcutaneously in two divided dosage of 30 mg each. Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

EXAMPLE 2

Optimized Hamster Reg3 Gamma Peptide Used for Insulin Independence Among Type 2 Diabetes Thirty milligrams of Optimized Reg3 gamma peptide (each of SEQ ID NOS:2-7) will be given subcutaneously per day will be given in two divided (15 mg per dosage) for children less than 11 years old weighing 66 pounds or less, and for children older than 11 years and weighing more than 66 pounds. Optimized hamster Reg3 gamma peptide (each of SEQ ID NOS:2-7) will be dosed as 60 mg per day subcutaneously given in two divided dosage of 30 mg each to results in insulin independence. For adults, optimized hamster Reg3 gamma peptide will be given as 60 mg twice daily subcutaneously resulting in insulin independence. Exogenous insulin dosages, whether by injection or pump are decreased based on glucose levels before meals and fasting. Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

Based upon glucose levels, other diabetes agents such as sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal.

EXAMPLE 3

Optimized Hamster Reg3 Gamma Peptide Used for Reducing Diabetes Medications Requirements Among Type 2 Diabetes Optimized hamster Reg3 gamma peptide (each of SEQ ID NOS:2-7) will be dosed at 30 mg per day given in two divided (15 mg per dosage) for children less than 11 years old weighing 66 pounds or less, and for children older than 11 years and weighing more than 66 pounds optimized hamster Reg3 gamma peptide (each of SEQ ID NOS:2-7) will be dosed as 60 mg per day given in two divided dosage of 30 mg subcutaneously to results in insulin independence. For adults, optimized hamster Reg3 gamma peptide (each of SEQ ID NOS:2-7) will be given as 60 mg twice daily by subcutaneous injection. Optimized hamster Reg3 gamma peptide (each of SEQ ID NOS:2-7) given in divided dosages in one capsule/pill or in on oral suspension may result in the need to diminish dosages of other diabetes medications utilized and such medications may potentially be tapered off. Medications include: sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal. Modifications made to the diabetes medication regimen will be made based on whether the patient glucose levels and the need to adjust the basal or postprandial agent will be made.

EXAMPLE 4

Optimized Hamster Reg3 Gamma Peptide Used for Drug Naive Type 2 Diabetes

Optimized hamster Reg3 gamma peptide (each of SEQ ID NOS:2-7) dosed at 30 mg per day given in two divided (15 mg per dosage) for children less than 11 years old weighing 66 pounds or less. For children older than 11 years and weighing more than 66 pounds, optimized hamster Reg3 gamma peptide (each of SEQ ID NOS:2-7) will be dosed as 60 mg per day given in two divided dosage of 30 mg each and may be delivered subcutaneously to results in insulin independence. For adults, optimized hamster Reg3 gamma peptide will be given as 60 mg twice daily by mouth in pill or oral suspension. Optimized hamster Reg3 gamma peptide (each of SEQ ID NOS:2-7) given in divided dosages in one capsule/pill or in on oral suspension results in normalization of blood glucose as measured by fasting glucose and hemoglobin A1C levels. Among a newly diagnosed or previously diagnosed type 2 diabetes patient who is currently on no pharmaceutical treatment for diabetes, optimized hamster Reg3 gamma peptide (each of SEQ ID NOS:2-7) is utilized among patients with type 2 diabetes with a primary endpoint of glucose levels and Hemoglobin A1C in the normal range with the glucose goals would be 100 mg/dL range before meals and 140 mg/dL two hours after meals.

EXAMPLE 5

Optimized Hamster Reg3 Gamma Peptide Used for Ex Vivo Generation of Beta Cells and Provided to Patients with Labile Type 1 with Cyclosporine for Insulin Independence and Type 2 Diabetes for Insulin Independence without an Immune Tolerance Agent Required Optimized hamster Reg3 gamma peptide (each of SEQ ID NOS:2-7) and/or agents that bind to the human Reg Receptor are used for the ex vivo transformation of new beta cells from pluripotent stem cells including embryonic cells, adult somatic stem cells, human adult bone-marrow derived stem cells, umbilical cord stems cells, mesenchymal stem cells, human amniotic membrane-derived mesenchymal cells, mammalian stem cells, mammalian stem cells, ectodermal stem cells or other stem cells and may include resident populations of endogenous stem cells that exist within the adult pancreas. The new beta cells are then administered to patients with new and existing type 1 and 2 diabetes, PreDiabetes or diseases of insulin deficiency, beta cell deficiency, insulin resistance and impaired glucose metabolism, with routes of delivery to include, but are not limited to the portal and umbilical vein, oral, intravenous, subcutaneous delivery with and without organ specific targeting and may include direct administration to the pancreas or liver. Patients receiving ex vivo formulated beta cells will require an immune tolerance agent to prevent autoimmune attack of the newly received beta cells. For example, patients will receive 7.5 mg/kg/day of Cyclosporine in divided dosages prior to receiving the ex vivo generated beta cells with dosages of Cyclosporine adjusted based upon peak and trough levels to optimize efficacy and reduce risks of side effects.

What is claimed is:

1. A pharmaceutical composition for treating diabetes comprising:
    a peptide comprising SEQ ID NO: 4; and
    oral interferon alpha.

2. The pharmaceutical composition of claim 1, wherein the composition is formulated for systemic administration.

3. The pharmaceutical composition of claim 1, wherein the composition comprises a targeting agent for targeted administration to specific locations, receptors, cells, tissues, organs, or organ systems.

* * * * *